(12) United States Patent
Stayman et al.

(10) Patent No.: US 7,632,015 B2
(45) Date of Patent: Dec. 15, 2009

(54) CT SCANNER INCLUDING DEVICE TO VISUALLY INDICATE AREA OF CT SCAN

(75) Inventors: Joseph Webster Stayman, Ann Arbor, MI (US); Miodrag Rakic, Redondo Beach, CA (US); David Phillipe Sarment, Ann Arbor, MI (US); Michael Thomas Kusner, Jr., Perrysburg, OH (US)

(73) Assignee: Xoran Technologies, Inc., Ann Arbor, MI (US)

( * ) Notice: Subject to any disclaimer, the term of this patent is extended or adjusted under 35 U.S.C. 154(b) by 88 days.

(21) Appl. No.: 12/021,526

(22) Filed: Jan. 29, 2008

(65) Prior Publication Data
US 2008/0181359 A1    Jul. 31, 2008

Related U.S. Application Data

(60) Provisional application No. 60/898,041, filed on Jan. 29, 2007.

(51) Int. Cl.
*A61B 6/08* (2006.01)
(52) U.S. Cl. .................. 378/206; 378/63; 378/163; 378/195
(58) Field of Classification Search ............ 378/4, 378/20, 63, 163, 195–198, 205, 206
See application file for complete search history.

(56) References Cited

U.S. PATENT DOCUMENTS

| | | | |
|---|---|---|---|
| 4,117,337 A * | 9/1978 | Staats ........................ 378/17 |
| 4,242,587 A | 12/1980 | Lescrenier | |
| 4,293,771 A | 10/1981 | Lescrenier | |
| 4,296,329 A * | 10/1981 | Mirabella ................ 250/491.1 |
| 4,538,289 A * | 8/1985 | Scheibengraber ............ 378/20 |
| 5,537,453 A * | 7/1996 | Williams et al. ............. 378/206 |
| 5,577,095 A * | 11/1996 | Kobayashi ................... 378/206 |
| 5,598,269 A * | 1/1997 | Kitaevich et al. ............ 356/399 |
| 5,690,107 A * | 11/1997 | Hofmann ..................... 600/407 |
| 6,044,291 A * | 3/2000 | Rockseisen ................ 600/429 |
| 6,048,097 A * | 4/2000 | Heinze ........................ 378/206 |
| 6,217,214 B1 * | 4/2001 | Cabral et al. ................. 378/196 |
| 6,810,595 B2 | 11/2004 | Chan | |
| 6,917,666 B2 | 7/2005 | Wollenweber | |
| 7,147,371 B2 * | 12/2006 | Hecker ........................ 378/206 |
| 2004/0258210 A1 * | 12/2004 | Ritter .......................... 378/198 |

* cited by examiner

Primary Examiner—Edward J Glick
Assistant Examiner—Thomas R Artman
(74) Attorney, Agent, or Firm—Carlson, Gaskey & Olds

(57) ABSTRACT

A first laser device and a second laser device direct a laser beam towards a patient before a CT scan to visually indicate an outer boundary of an area where x-rays will be directed during the CT scan. Each laser device includes a prism that deflects the laser beams to form lines on the patient that define an outer boundary of an area of the patient that will be exposed to the x-rays. If the area of the patient between the lines is not the desired area, the operator can move the patient until the desired area of the patient is located between the lines. A third laser device can direct a laser beam to define an outer boundary that is used to ensure proper orientation of the patient in the space.

10 Claims, 5 Drawing Sheets

CT SCANNER INCLUDING DEVICE TO VISUALLY INDICATE AREA OF CT SCAN

REFERENCE TO RELATED APPLICATIONS

This application claims priority to U.S. Provisional Patent Application No. 60/898,041 filed Jan. 29, 2007.

BACKGROUND OF THE INVENTION

The present invention relates generally to a device that visually indicates where x-rays from a CT scanner are directed on a patient.

A CT scanner takes a plurality of x-ray images of a part of a patient to create a three dimensional CT image. As a gantry rotates about the patient P, a detector takes the plurality of x-ray images at a plurality of rotational positions. As the x-rays are invisible, an operator supervising the CT scan cannot determine where the x-rays are directed on the patient. If the patient is not positioned correctly in the CT scanner, the resulting three dimensional CT image would not represent an image of the desired area of the patient. The CT scan would need to be repeated, exposing the patient to additional x-rays.

SUMMARY OF THE INVENTION

A first laser device and a second laser device direct a laser beam on a patient before a CT scan to indicate where x-rays will be directed during the CT scan. Each laser device includes a prism that deflects the laser beams to form a line on the patient that visually indicates an outer boundary of an area of the patient that will exposed to the x-rays during the CT scan.

An area of interest is located in the area. Therefore, before the CT scan, the operator of the CT scanner can visually determine where the x-rays will be directed on the patient during the CT scan. If the area of the patient P between the lines is not the desired area, the operator can move the patient until the desired area of the patient is located between the lines. The lines can also be shown on the patient during the CT scan to indicate where the x-rays are being directed.

The CT scanner also includes a third laser device located on a cross-bar section of a gantry of the CT scanner that directs a laser beam that defines an upper boundary used to ensure proper orientation of the patient in the CT scanner.

The CT scanner can include a camera that captures an external image of the patient that is displayed on a display. A computer virtually projects lines on the external image to indicate where the x-rays will be directed on the patient during the CT scan. The computer is programmed such that the locations of the lines correlate to an outer boundary of an area where the x-rays will be directed to the patient.

These and other features of the present invention will be best understood from the following specification and drawings.

DETAILED DESCRIPTION OF THE PREFERRED EMBODIMENT

Figure 1:
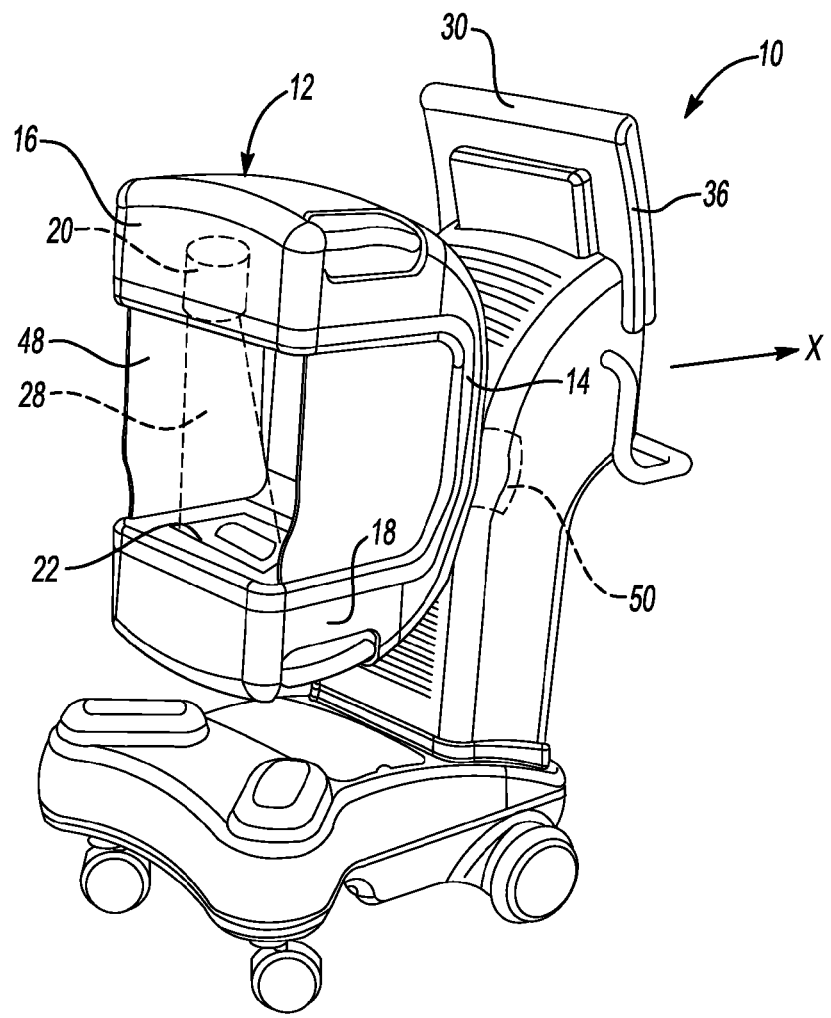
FIG. 1 schematically illustrates a first embodiment CT scanner.

FIG. 1 illustrates a CT scanner 10 of the present invention including a gantry 12 that supports and houses components of the CT scanner 10. In one example, the gantry 12 includes a cross-bar section 14, and a first arm 16 and a second arm 18 each extend substantially perpendicularly from opposing ends of the cross-bar section 14 to form the c-shaped gantry 12. The first arm 16 houses an x-ray source 20 that generate x-rays 28. In one example, the x-ray source 20 is a cone-beam x-ray source. The second arm 18 houses a complementary flat-panel detector 22. The x rays 28 are directed toward the detector 22 which includes a converter (not shown) that converts the x-rays 28 from the x-ray source 20 to visible light and an array of photodetectors behind the converter to create an image. As the gantry 12 rotates about the patient P, the detector 22 takes a plurality of x-ray images at a plurality of rotational positions. Various configurations and types of x-ray sources 20 and detectors 22 can be utilized, and the invention is largely independent of the specific technology used for the CT scanner 10.

Figure 2:
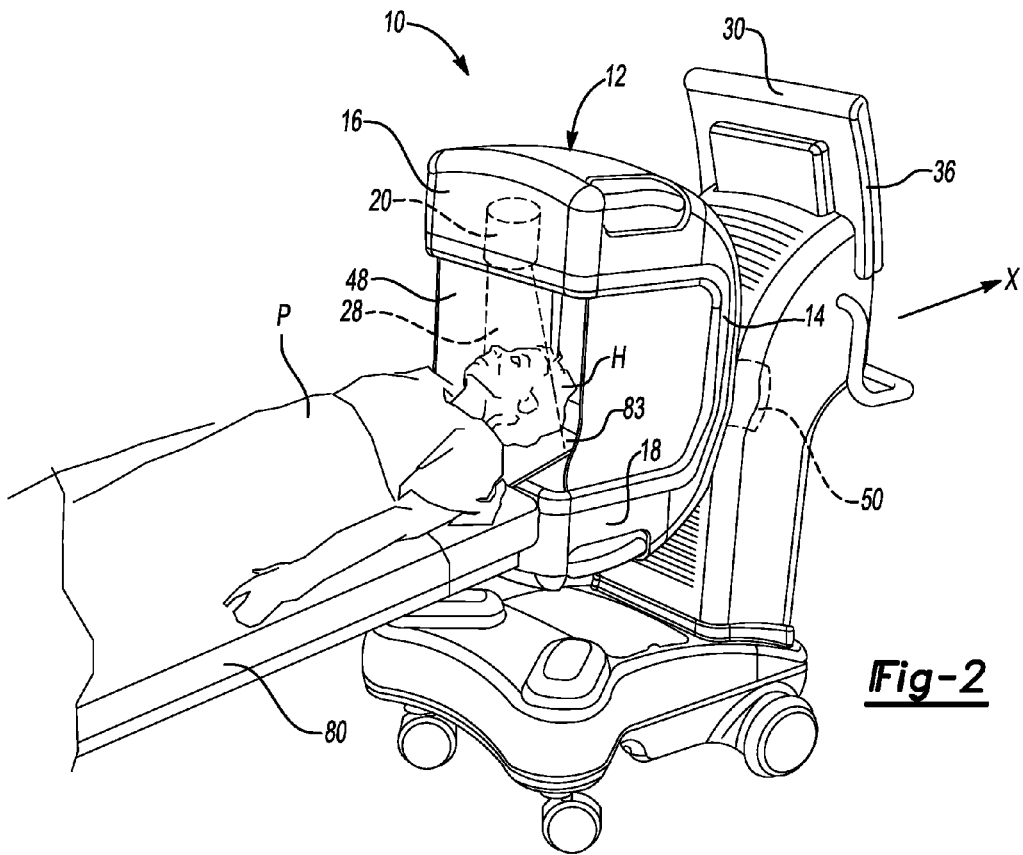
FIG. 2 illustrates the CT scanner of FIG. 1 with a part of a patient received in the CT scanner.
Figure 3:
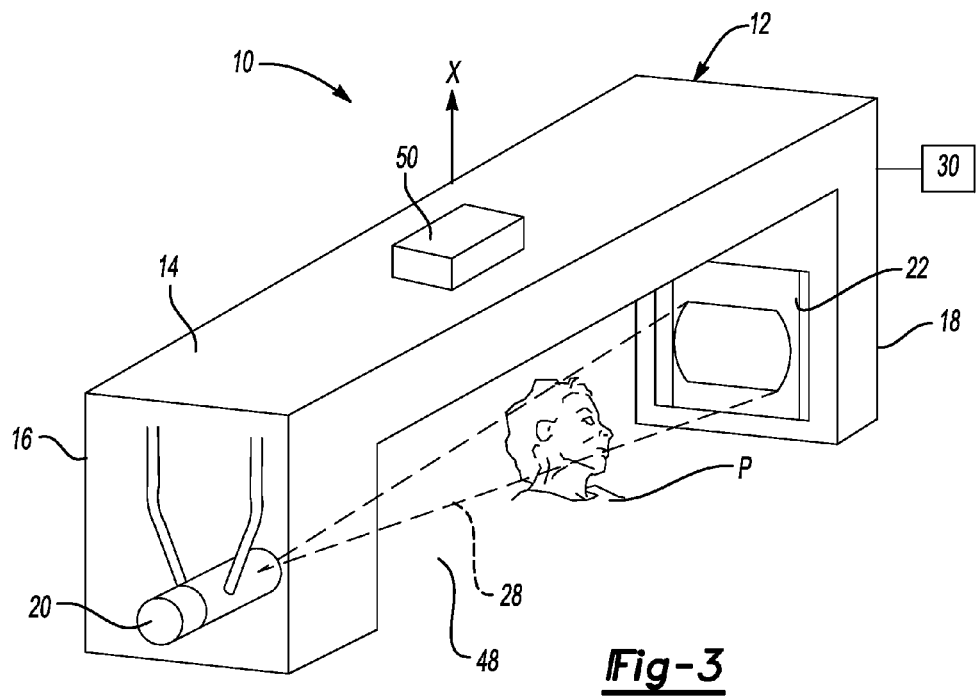
FIG. 3 illustrates a second embodiment of the CT scanner.

FIG. 2 illustrates the CT scanner 10 with a part of the patient P received in a space 48 between the first arm 16 and the second arm 18. A motor 50 rotates the gantry 12 about an axis of rotation X to obtain a plurality of x-ray images of the patient P at the plurality of rotational positions. The axis of rotation X is positioned between the x-ray source 20 and the detector 22. The gantry 12 can be rotated approximately slightly more than 360 degrees about the axis of rotation X. In one example, as shown in FIGS. 1 and 2, the axis of rotation X is substantially horizontal. In this example, the patient P is typically lying down on a table 70. The head H of the patient P rests on a headrest 83. Alternatively, as shown in FIG. 3, the axis of rotation X is substantially vertical. Typically, in this example, the patient P is sitting upright.

Figure 4:
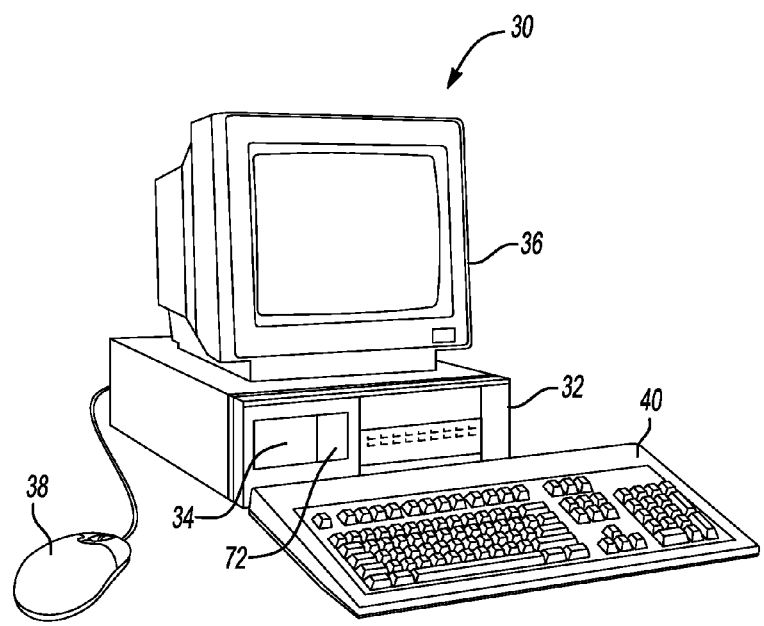
FIG. 4 illustrates a computer employed with the CT scanner.

As shown schematically in FIG. 4, the CT scanner 10 further includes a computer 30 having a microprocessor or CPU 32, a storage 34 (memory, hard drive, optical, and/or magnetic, etc), a display 36, a mouse 38, a keyboard 40 and other hardware and software for performing the functions described herein. The computer 30 powers and controls the x-ray source 20 and the motor 50. The plurality of x-ray images taken by the detector 22 are sent to the computer 30. The computer 30 generates a three-dimensional CT image from the plurality of x-ray images utilizing any known techniques and algorithms. The three-dimensional CT image is stored on the storage 34 of the computer 30 and can be displayed on the display 36 for viewing.

Figure 5:
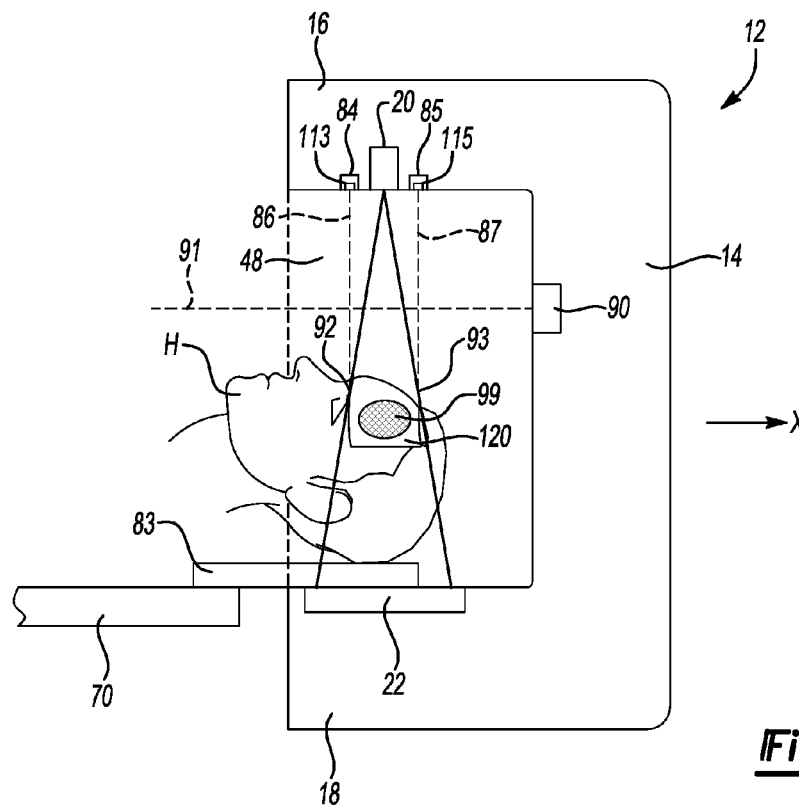
FIG. 5 illustrates a side view of the gantry of the CT scanner including laser devices that are used to visually indicate an imaging volume of the CT scan.

As shown in FIG. 5, the CT scanner includes a first laser device 84 and a second laser device 85 that each direct a laser beam 86 and 87, respectively, towards a part (such as the head H) of the patient P that is received in the space 48. FIG. 5 illustrates the CT scanner 10 of FIG. 1, but the CT scanner 10 of FIG. 3 operates in the same manner. Although the head H of the patient P is described, any part of the patient P can be located in the space 48.

Before the CT scan, the first laser device 84 and the second laser device 85 direct a laser beam 86 and 87, respectively, towards the patient P to indicate to the operator where the x-rays 28 will be directed during the CT scan. Each laser device 84 and 85 include a prism 113 and 115, respectively, that deflects the laser beams 86 and 87, respectively, to form planes that form lines 117 and 119, respectively, on the patient P (shown in FIG. 6) that visually indicate an imaging volume 120. However, any type of optic device can be used to defect the laser beams 86 and 87. In one example, the first laser device 84 and the second laser device 85 are located on the first arm 16 of the gantry 12, for example on each side of the x-ray source 20. The laser devices 84 and 85 are calibrated and positioned to direct the laser beams 86 and 87 such that they contact the patient P at opposing locations 92 and 93, respectively, and form a visual mark or line on the patient P, visually indicating an outer boundary of an area of the imaging volume 120 of the patient P.

Figure 6:
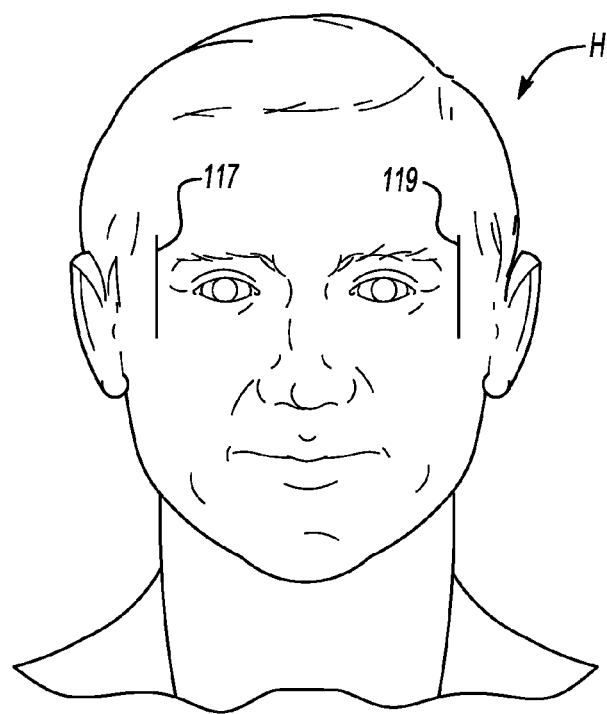
FIG. 6 illustrates a front view of a head of the patient including laser lines that indicate the imaging volume.

The locations 92 and 93 define the outer boundary of the area of the patient P exposed to the x-rays 28 and define the outer boundary of the imaging volume 120 or the area that will be shown in the three dimensional CT scan. An area of interest 99 is located in the imaging volume 120. As shown in FIG. 6, in one example, the laser beams 86 and 87 form substantially parallel lines 117 and 119, respectively, on the patient P to define the outer boundaries of the imaging volume 120. Therefore, before the CT scan, the operator of the CT scanner 10 can visually determine where the x-rays 28 will be directed on the patient P during the CT scan. If the area of the patient P between the laser beams 86 and 87 is not the desired area, the operator can move the patient P until the desired area of the patient P is located between the laser beams 86 and 87. The lines 117 and 119 can also be viewed on the patient P during the CT scan to determine that the CT scanner 10 is taking images of the proper part of the patient P.

Figure 7:
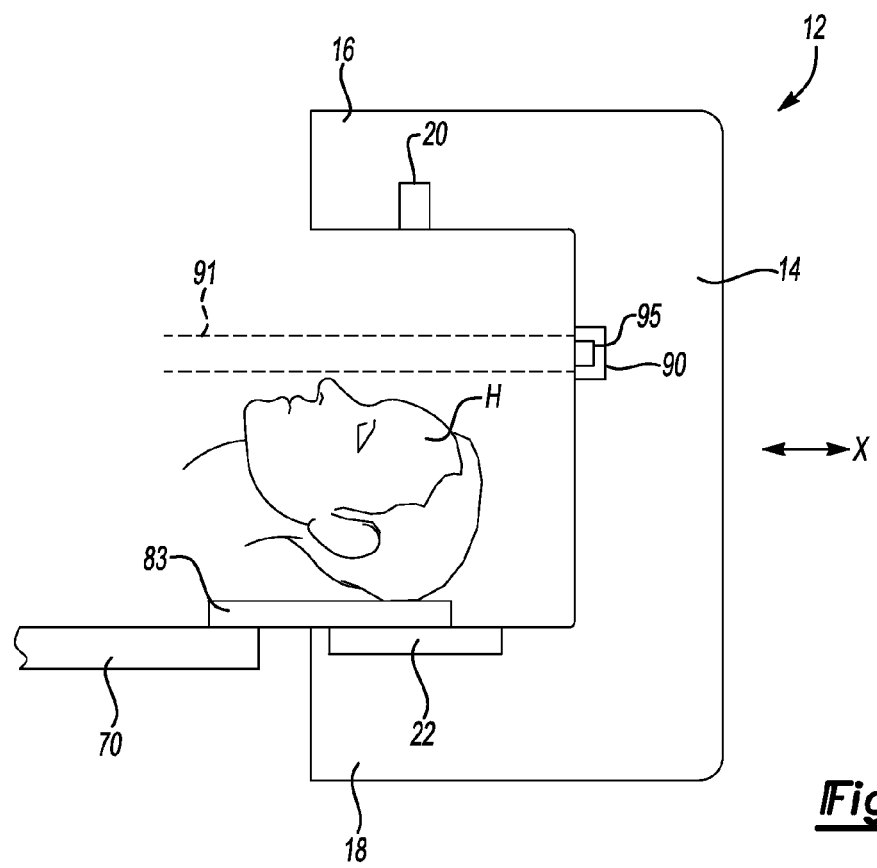
FIG. 7 illustrates a side view of the gantry of the CT scanner including a curved laser beam that is used to ensure the patient is properly positioned in the CT scanner.
Figure 8:
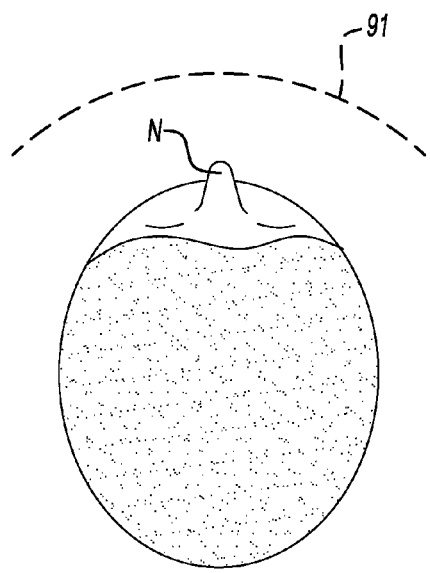
FIG. 8 illustrates a top view of the head of the patient in the gantry of the CT scanner of FIG. 7.

The CT scanner 10 can also include a third laser device 90 located on the cross-bar section 14 of the gantry 12 that directs a laser beam 91 that helps to ensure proper positioning of the patient P within the space 48. In one example, the laser beam 91 is substantially perpendicular to the laser beams 86 and 87 and substantially straight. Alternately, the laser beam 91 can be curved around the head H of the patient P, as shown in FIGS. 7 and 8. In this example, a prism 95 deflects the laser beam 91 to curve the laser beam 91 around the head H of the patient P. FIG. 8 shows a top view of the head H of the patient P. The laser beam 91 defines a front boundary that is used to ensure proper orientation of the patient P in the space 48. For example, as shown in FIGS. 5 and 7, the laser device 90 directs a laser beam 91 that does not contact the patient P. This indicates that the patient P is properly oriented in the space 48 in the CT scanner 10. If the laser beam 91 contacts the patient P, this indicates that the patient P is positioned too close to the x-ray source 20. If this occurs, a part of the patient P will get cut off during the CT scan as the gantry 12 rotates about the patient P. If the laser beam 91 contacts the patient P, this indicates that the patient P needs to be moved until the laser beam 91 no longer contacts the patient P. Once the patient P is properly positioned in the CT scanner 10, a CT scan can be performed.

Figure 9:
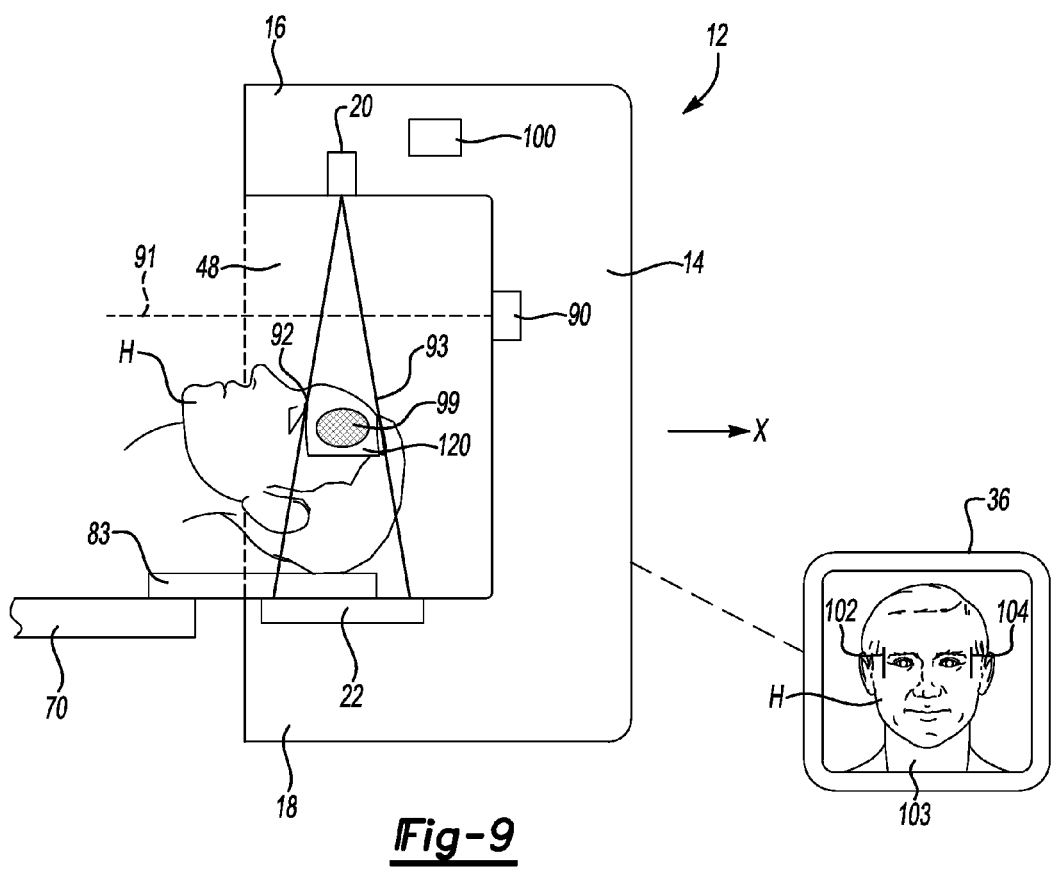
FIG. 9 illustrates a side view of the gantry of the CT scanner including a camera that is used to visually indicate the area of the CT scan.

In another example, as shown in FIG. 9, the CT scanner 10 includes a camera 100 instead of the laser devices 84 and 85. Before the CT scan, the camera 100 captures an external image 103 of the patient P that is displayed on the display 36.

The computer 30 virtually projects parallel lines 102 and 104 on the external image 103 to indicate an outer boundary of an area where the x-rays 28 will be directed on the patient P during the CT scan. The computer 30 is programmed such that the locations of the lines 102 and 104 on the patient P correlate to the outer boundaries of the locations 92 and 93 where the x-rays 28 will be directed to the patient P. The area between the lines 102 and 104 represents the imaging volume 120 or the outer boundary of the area of the patient P that will be shown in the three dimensional CT image. The lines 102 and 104 can also be shown on the external images 103 during the CT scan.

If the area of the patient P between the lines 102 and 104 is not the desired area, the x-rays 28 will be directed to an improper location, resulting in a three dimensional CT image of a wrong area of the patient P. The operator can adjust the positioning of the patient P in the space 48 of the CT scanner 10 so that a CT scan of the desired area of the patient P can be taken, reducing the likelihood that a second CT scan is needed. Once the patient P is properly positioned in the CT scanner 10, the CT scanner 10 is operated to obtain the three dimensional CT image.

The foregoing description is only exemplary of the principles of the invention. Many modifications and variations are possible in light of the above teachings. It is, therefore, to be understood that within the scope of the appended claims, the invention may be practiced otherwise than using the example embodiments which have been specifically described. For that reason the following claims should be studied to determine the true scope and content of this invention.

What is claimed is:

1. A CT scanner assembly comprising:
a CT scanner including an x-ray source to generate x-rays and an x-ray detector mounted opposite the x-ray source;
a device to generate spaced apart markers indicating an area on the patient where the x-rays are to be directed during a CT scan, wherein the device is a camera that captures an external image of the patient that is displayed on a display and the spaced apart markers are lines; and
a computer virtually projects the lines on the external image to indicate the area on the patient where the x-rays will be directed during the CT scan.

2. A CT scanner comprising:
a gantry including a cross-bar section, a first arm and a second arm that each extend substantially perpendicularly to the cross-bar section;
an x-ray source housed in the first arm;
an x-ray detector housed in the second arm to generate a plurality of x-ray images;
a laser device housed in the cross-bar section that directs a laser beam to determine a proper location of the patient; and
a device to generate spaced apart markers indicating an area on the patient where the x-rays are to be directed during a CT scan.

3. The CT scanner as recited in claim 2 wherein the laser beam is substantially straight.

4. The CT scanner as recited in claim 2 further including a prism, wherein the prism curves the laser beam.

5. The CT scanner as recited in claim 2 wherein the patient is to be moved if the laser beam contacts the patient.

6. The CT scanner as recited in claim 2 wherein the spaced apart markers are laser marks on the patient, and the device comprises a first laser device and a second laser device that direct a first laser beam and a second laser beam, respectively, towards the patient to form one of the laser marks.

7. The CT scanner as recited in claim 6 wherein the laser marks are substantially parallel lines, and a prism deflects each of the first laser beam and the second laser beam to form the substantially parallel lines.

8. The CT scanner as recited in claim 6 wherein the first laser device and the second laser device are located on the first arm.

9. The CT scanner as recited in claim 2 wherein the device is a camera that captures an external image of the patient that is displayed on a display and the spaced apart markers are lines, and a computer virtually projects the lines on the external image to indicate the area on the patient where the x-rays will be directed during the CT scan.

10. A method of determining an area on a patient where x-rays are to be directed the method comprising the steps of:
generating spaced apart markers indicating an area on a patient where x-rays are to be directed during a CT scan;
performing the CT scan of the patient; and
capturing an external image of the patient, and the step of generating the spaced apart markers includes projecting lines on the external image to indicate the area on the patient where the x-rays will be directed during the CT scan and displaying the external image including the lines.

* * * * *